US007781410B2

(12) United States Patent
Saliou et al.

(10) Patent No.: US 7,781,410 B2
(45) Date of Patent: Aug. 24, 2010

(54) COMPOSITIONS CONTAINING CHALCONES AND USE THEREOF

(75) Inventors: Claude Saliou, Bernardsville, NJ (US); Sekhar Boddupalli, Palo Alto, CA (US); Khalid Mahmood, Palo Alto, CA (US); Michael Anthonavage, Lebanon, NJ (US); Kelly Huang, New Hope, PA (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 405 days.

(21) Appl. No.: 11/462,390

(22) Filed: Aug. 4, 2006

(65) Prior Publication Data

US 2008/0032938 A1 Feb. 7, 2008

(51) Int. Cl.
*A61K 31/353* (2006.01)

(52) U.S. Cl. ........................... 514/25; 514/32; 514/859

(58) Field of Classification Search .................. 514/25, 514/32, 859
See application file for complete search history.

(56) References Cited

U.S. PATENT DOCUMENTS 4,514,385 A 4/1985 Damani et al.
6,462,075 B1 10/2002 Bowen et al.
2005/0148599 A1 7/2005 Bowen et al.
2006/0212025 A1 * 9/2006 McDaniel ...................... 606/9

FOREIGN PATENT DOCUMENTS

KR 2003/0076558 A 9/2003
WO WO 99/47119 A 9/1999

OTHER PUBLICATIONS

Entry for acne, The Merck manual Online Medical Library, last revised Feb. 2003, accessed online at www.merck.com on Jul. 8, p. 2, paragraph 5-7.
Nishino et al, "Antibacterial Activity of Flavonoids against Staphylococcus epidermidis, a Skin Bacterium", Agric. Biol. Chem., vol. 51, No. 1 (1987) pp. 139-143.
Haddad et al, "Novel Antiproliferative Flavonoids Induce Cell Cycel Arrest in Human Prostate Cancer Cell Lines", Prostate Cancer and Prostatic Diseases, vol. 9 (2006) pp. 68-76, published online Nov. 29, 2005.
Falcocchio, S. et al., "Propionibacterium acnes GehA lipase, an enzyme involved in acne development, can be successfully inhibited by defined natural substances", Journal of Molecular Catalysis. B, Enzymatic, Elsevier, Amsterdam, NL, vol. 40, No. 3-4, Jun. 1, 2006, pp. 132-137, XP025156483.

* cited by examiner

*Primary Examiner*—Shaojia Anna Jiang
*Assistant Examiner*—Everett White

(57) ABSTRACT

The present invention features composition comprising a chalcone and the use thereof for treating acne and reducing the appearance of oil or pores on the skin, hair and scalp.

7 Claims, No Drawings

COMPOSITIONS CONTAINING CHALCONES AND USE THEREOF

BACKGROUND OF THE INVENTION

Acne disorders are often classified as noninflammatory or inflammatory types. Noninflammatory acne is characterized by closed comedones (whiteheads) and open comedones (blackheads), consisting of compact masses of keratin, sebum, and bacteria, which dilate the follicular duct. A comedone forms when a pilo-sebaceous duct is obstructed and/or when there is increased production of sebum by a sebaceous gland. Formation of the comedone can be followed by inflammation, resulting from bacterial proliferation and/or overproduction of sebum. Typically, the bacteria are anaerobic bacteria such as Propionibacteria (P. acnes). Inflammatory acne is characterized by papules (pimples), pustules, and nodulocystic lesions, which may lead to scarring. Several factors are believed to play important roles in the pathogenesis of acne including: sebum production, hormonal stimulation, plugged pores, and skin pathogens. Sebum levels are increased in subjects with acne by approximately 70% compared to sebum levels of control subjects.

The present invention relates to the unexpected discovery that certain chalcones are topically effective for treating acne and reducing the appearance of oil or pores on the skin.

SUMMARY OF THE INVENTION

In one aspect, the present invention features a method of treating acne or reducing the appearance of oil or pores on the skin by administering to skin in need of such treatment a composition including a chalcone of Formula I Formula I

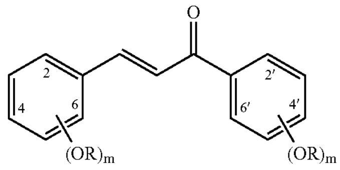

wherein,

R is hydrogen, $C_1$-$C_6$ alkyl, $C_2$-$C_{10}$ alkenyl, acyl or glycosyl, and m is 0 to 5; and n is 0 to 5;

or a cosmetically-acceptable salt thereof; provided that the sum of m and n is greater than or equal to 4.

In one aspect, the present invention features a method of treating acne or reducing the appearance of oil or pores on the skin by administering to skin in need of such treatment a composition comprising (a) a chalcones of Formula I Formula I

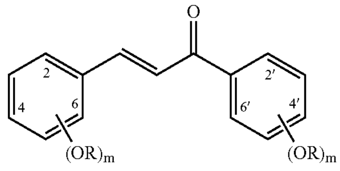

wherein,

R is hydrogen, $C_1$-$C_6$ alkyl, $C_2$-$C_{10}$ alkenyl, acyl or glycosyl, and m is 0 to 5;

n is 0 to 5;

or a cosmetically-acceptable salt thereof; and (b) a catechin.

In another aspect, the present invention features a product including (a) such a composition and (b) instructions directing the user to administer said composition to skin in order to treat acne or reduce the appearance of oil or pores on the skin.

In another aspect, the present invention features a method of promoting such a composition by directing the user to administer said composition to skin in order to treat acne or reduce the appearance of oil or pores on the skin.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W)).

Definitions

What is meant by "treating acne" is reducing or preventing acne or rosacea.

What is meant by a "product" is a product in finished packaged form. In one embodiment, the package is a container such as a plastic, metal or glass tube or jar containing the composition. The product may further contain additional packaging such as a plastic or cardboard box for storing such container. In one embodiment, the product contains instructions directing the user to apply the composition to (i) treat acne or (ii) reduce the appearance of oil or pores on the skin.

What is meant by "promoting" is promoting, advertising, or marketing. Examples of promoting include, but are not limited to, written, visual, or verbal statements made on the product or in stores, magazines, newspaper, radio, television, internet, and the like.

For promoting the treatment of acne, examples of such statements include, but are not limited to, "treats acne," "prevents acne," "reduces acne lesions, comedones, or pimples," "reduces the appearance of acne lesions, comedones, or pimples," "reduces the appearance of acne breakouts and blemishes," "preventing, controlling or regulating the appearance of acne breakouts and blemishes", and "reduces breakouts and blemishes."

For promoting the reduction in the appearance of oil on the skin, examples of such statements include, but are not limited to, "reduces the appearance of sebum," "preventing, controlling or regulating the production of sebum," "reduces sebum," "reduces the appearance of oily/shiny skin," "reduces the appearance of greasy skin," and "reduces shine on the skin, hair, or scalp." In one embodiment, the composition is applied to skin not in need of treatment for acne (i.e., skin not suffering from acne or the scalp/hair).

For promoting the reduction in the appearance of pores on the skin, examples of such statements include, but are not limited to, "reduces the size of pores,""minimizes the appearance of pores," "refines the appearance of pores," "reduces the visibility or pores," and "closes pore opening." In one embodiment, the composition is applied to skin not in need of treatment for acne (i.e., skin not suffering from acne).

As used herein, "administering to skin in need of such treatment" means contacting (e.g., by use of the hands or an applicator such, but not limited to, a wipe, tube, roller, spray, or patch) the area of skin in need such treatment or an area of skin proximate to the area of skin in need of such treatment.

As used herein, "composition" means a composition suitable for administration to the skin.

As used herein, "cosmetically-acceptable" means that the ingredients which the term describes are suitable for use in contact with the skin without undue toxicity, incompatibility, instability, irritation, allergic response, and the like.

As used herein, "safe and effective amount" means an amount of the compound, carrier, or of the composition sufficient to induce an enhancement in tissue elasticity, but low enough to avoid serious side effects. The safe and effective amount of the compounds or composition will vary with the area being treated, the age, health and skin type of the end user, the duration and nature of the treatment, the specific compound or composition employed, the particular cosmetically-acceptable carrier utilized, and like factors.

Compounds

The compositions of the present invention contain at least one compound of the formula I a chalcone of Formula I Formula I

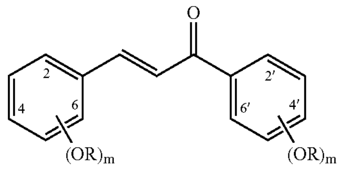

wherein,

R is hydrogen, $C_1$-$C_6$ alkyl, $C_2$-$C_{10}$ alkenyl, acyl or glycosyl, and m is 0 to 5; and n is 0 to 5;

or a cosmetically-acceptable salt thereof.

In one embodiment, the sum of m and n is greater than or equal to 4 (such as equal to 4, 5 or 6)

Examples of compounds of formula I include, but are not limited to, those compounds set forth below in Table 1 of Example 1.

The compounds of the present invention may also be present in the form of cosmetically acceptable salts. For use in medicine, the salts of the compounds of this invention refer to non-toxic "cosmetically acceptable salts," cosmetically acceptable acidic/anionic or basic/cationic salts. Cosmetically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Cosmetically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc. Other salts may, however, be useful in the preparation of compounds according to this invention or of their cosmetically acceptable salts. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

In one embodiment, the compositions of present invention contain from about 0.01% to about 10% by weight of such compound, such as from about 0.1% to about 5% by weight of such compound, such as from about 0.5% to about 3% by weight of such compound. In one embodiment, the composition contains at least 1% by weight of such compound, such as at least about 2% by weight of such compound. The compounds of the invention may be synthesized by those having ordinary skill in the art and/or purchased from commercial sources such as Indofine Chemicals Inc. (Somerville, N.J.).

Compositions

The compositions useful in the present invention involve formulations suitable for administering to the target tissues, such as mammalian skin such as human skin. In one embodiment, the composition contains a safe and effective amount of (i) a chalcone of formula I and (ii) a cosmetically-acceptable carrier. In one embodiment, the cosmetically-acceptable carrier is from about 50% to about 99.99%, by weight, of the composition (e.g., from about 80% to about 99%, by weight, of the composition).

The compositions may be made into a wide variety of product types that include but are not limited to solutions, suspensions, lotions, creams, gels, toners, sticks, sprays, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks, make-up such as foundations, eye liners, and eye shadows, and the like. These product types may contain several types of cosmetically-acceptable carriers including, but not limited to, solutions, suspensions, emulsions such as microemulsions and nanoemulsions, gels, solids and liposomes. The following are non-limitative examples of such carriers. Other carriers can be formulated by those of ordinary skill in the art.

The compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include: propylene glycol, polyethylene glycol (200-600), polypropylene glycol (425-2025), glycerol, 1,2,4-butanetriol, sorbitol esters, 1,2,6-hexanetriol, ethanol, and mixtures thereof.

A lotion can be made from such a solution. Lotions typically contain from about 1% to about 20% (e.g., from about 5% to about 10%) of an emollient(s) and from about 50% to about 90% (e.g., from about 60% to about 80%) of water. As used herein, "emollients" refer to materials used for the prevention or relief of dryness, as well as for the protection of the skin or hair. Examples of emollients include, but are not limited to, those set forth in the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7th Edition, 1997) (hereinafter "ICI Handbook").

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may contain a simple base of animal, vegetable, or synthetic oils or semi-solid hydrocarbons. An ointment may contain from about 2% to about 10% of an emollient(s) plus from about 0.1% to about 2% of a thickening agent(s). Examples of thickening agents include, but are not limited to, those set forth in the ICI Handbook pp. 1693-1697.

The compositions useful in the present invention can also be formulated as emulsions. If the carrier is an emulsion, from about 1% to about 10% (e.g., from about 2% to about 5%) of the carrier contains an emulsifier(s). Emulsifiers may be nonionic, anionic or cationic. Examples of emulsifiers include, but are not limited to, those set forth in the ICI Handbook, pp. 1673-1686.

Lotions and creams can be formulated as emulsions. Typically such lotions contain from 0.5% to about 5% of an emulsifier(s), while such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, soap bar composition, powder, and wipe containing powder).

The compositions useful in the subject invention may contain, in addition to the aforementioned components, a wide variety of additional oil-soluble materials and/or water-soluble materials conventionally used in compositions for use on skin at their art-established levels.

Additional Cosmetically Active Agents

In one embodiment, the composition further contains another cosmetically active agent in addition to the above compounds. What is meant by a "cosmetically active agent" is a compound (e.g., a synthetic compound or a compound isolated from a natural source, or a natural extract containing a mixture of compounds) that has a cosmetic or therapeutic effect on the tissue, including, but not limiting to, lightening agents, darkening agents such as self-tanning agents, anti-acne agents, shine control agents, anti-microbial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, anti-callous agents, agents for skin conditioning, anti-cellulite agents, fluorides, and odor-control agents such as odor masking or pH-changing agents.

In one embodiment, the cosmetically active agent is selected from, but not limited to, the group consisting of hydroxy acids, benzoyl peroxide, D-panthenol, octyl methoxycinnimate, titanium dioxide, octyl salicylate, homosalate, avobenzone, carotenoids, free radical scavengers, spin traps, retinoids and retinoid precursors such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, amino acids such a proline, vitamins, lactobionic acid, acetyl-coenzyme A, niacin, riboflavin, thiamin, ribose, electron transporters such as NADH and FADH2, and other botanical extracts such as aloe vera, Feverfew, and Soy, and derivatives and mixtures thereof. The cosmetically active agent will typically be present in the composition of the invention in an amount of from about 0.001% to about 20% by weight of the composition, e.g., about 0.005% to about 10% such as about 0.01% to about 5%.

Examples of vitamins include, but are not limited to, vitamin A, vitamin Bs such as vitamin B3, vitamin B5, and vitamin B12, vitamin C, vitamin K, vitamin E such as alpha, gamma or delta-tocopherol, and derivatives (such as salts and esters) and mixtures thereof.

Examples of hydroxy acids include, but are not limited, to glycolic acid, lactic acid, malic acid, salicylic acid, citric acid, and tartaric acid.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), different types of tocopherols (e.g., alpha-, gamma-, and delta-tocopherols and their esters such as acetate) and their mixtures, tocotrienols, and ubiquinone. Natural extracts containing antioxidants suitable for use in the compositions of this invention, include, but not limited to, extracts containing flavonoids, isoflavonoids, and their derivatives such as genistein and diadzein (e.g., such as Soy and Clover extracts, extracts containing resveratrol and the like. Examples of such natural extracts include grape seed, green tea, pine bark, and propolis.

Examples of enzymes include, but are not limited to, proteases such as fungal proteases, bacterial proteases or mammalian proteases. Examples of such proteases include, but are not limited to, pepsin, cathepsin, human urinary acid protease, fungal proteases derived from *Neurospora oryzae, Mucor pusillus, Mucor miehei, Rhizopus chinensis*, or *Endothia parasitica*, and bacterial proteases rhizopuspepsin, penicillopepsin, and endothiapepsin. Further, the proteases may be derived from processes involving genetic engineering processes and techniques.

Examples of fungal extracts include, but are not limited to, extracts from *Neurospora oryzae, Mucor pusillus, Mucor miehei, Rhizopus chinensis*, or *Endothia parasitica Mucor Miehei*. Examples of compositions containing such proteases and fungal extracts are disclosed in U.S. Pat. No. 5,976,556.

Anti-acne Agents

In one embodiment, the present invention relates to topical compositions including an anti-acne agent. What is meant by an anti-acne agent is an compound that has been approved by the U.S. Food and Drug Administration for the topical treatment of acne. Examples of anti-acne agents include, but are not limited to, salicylic acid, benzoyl peroxide, sulphur, retinoic acid, candida bombicola/glucose/methyl rapeseedate ferment, peat water, resorcinol, silt, peat, permethin, azelaic acid, clindamycin, adapalene, erythromycin, sodium sulfacetamide, and combinations thereof. In one embodiment, the amount of anti-acne agent in the composition is from about 0.01% to about 10%, for example from about 0.1% to about 5%, or from about 0.5% to about 2% by weight, based on the total weight of the composition.

Catechins

In one embodiment, the compositions of the present invention further contain a catechin. The term "catechin" refers to a polyphenolic substance that belongs to the flavan-3-ol class of flavonoids. The catechins may be synthetically made or naturally made (e.g., such as part of a plant extract). Exemplary catechins include but are not limited to, catechin (C), catechin gallate (CG), epicatechin (EC), gallocatechin (GC), gallocatechin gallate (GCG), epigallocatechin (EGC), epicatechin gallate (ECG), and epigallocatechin gallate (EGCG). Exemplary plants which have a content of catechins include but are not limited to Catechu, Green Tea (*Camellia sinensis, Camellia oleifera*), *Vitis vinifera*, grape (*Vitis vinifera*), agrimony (*Agrimonia eupatoria*), cotton (*Gossypium* sp), black currant (*Ribes nigrum*), cowberry (*Vaccinium vitis-idaea* var. *minus*), *Alpinia galanga* and *Alpinia katsumada*. Catechins can be synthetically made or are available commercially, for example from Indofine (Somerville, N.J.) or from Aldrich (Milwaukee, Wis.).

Plant Extract

In one embodiment, the compositions of present invention further contain another plant extract. What is meant by a "plant extract" is a blend of compounds isolated from a plant. Such compounds may be isolated from one or more part of the plant (e.g., the whole plant, flower, seed, root, rhizome, stem, fruit and/or leaf of the plant) by physically removing a piece of such plant, such as grinding a flower of the plant. Such compounds may also be isolated from the plant by using extraction procedures well known in the art (e.g., the use of organic solvents such as lower $C_1$-$C_8$ alcohols, $C_1$-$C_8$ alkyl polyols, $C_1$-$C_8$ alkyl ketones, $C_1$-$C_8$ alkyl ethers, acetic acid $C_1$-$C_8$ alkyl esters, and chloroform, and/or inorganic solvents such as water, inorganic acids such as hydrochloric acid, and inorganic bases such as sodium hydroxide).

In one embodiment, the plant extract (e.g., an alpinia extract, a green tea extract, a feverfew extract, an agrimony extract, a cotton extract, a grape extract, a black currant extract, a cowberry extract or a soybean extract) is present in the composition in an amount from about 0.001% to about 20% by weight, in particular in an amount from about 0.1% to about 10% by weight of the composition. Unless stated otherwise, the weight of the extract refers to the dry weight of the extract.

Feverfew Extract

In one embodiment, the compositions of present invention further contain a feverfew extract. What is meant by a "feverfew extract" is a blend of compounds isolated from a feverfew plant. Examples of such compounds, include, but are not limited to, apigenin-7-glucoside, apigenin-7-glucuronide, 1-β-hydroxyarbusculin, 6-hydroxykaempferol-3,7-4'-trimethylether (Tanetin), 6-hydroxykaempferol-3,7-dimethyl ether, 8-β-reynosin, 10-epicanin, ascorbic acid, beta-carotene, calcium, chromium, chrysanthemolide, chrysanthemomin, chrysarten-A, chrsyarten-c, chrysoeriol-7-glucuronide, cobalt, cosmosiin, epoxyartemorin, luteolin-7-glucoside, luteolin-7-glucuronide, mangnoliolide, parthenolide, quercetagentin-3,7,3'-trimethylether, quercetagetin-3'7-dimethylether, reynosin, tanaparthin, tanaparthin-1α,4α-epoxide, tanaparthin-1β,4β-epoxide, β-costunolide, 3-β-hydroxy-parthenolide, and 3,7,3'-trimethoxyquercetagetin. The α-unsaturated γ-lactones present in the feverfew plant, such as parthenolide, are known to cause the allergic reactions. Therefore, in one embodiment, the feverfew extract is substantially free of the allergy causing α-unsaturated γ-lactones. The preparation of feverfew extract that is substantially free of parthenolide is disclosed in Example 1 in U.S. Patent Application No. 20040105905.

Soybean Extract

In one embodiment, the compositions of present invention further contain a soybean extract. What is meant by a "soybean extract" is a blend of compounds isolated from soybean. The soybean extract may contain only a portion of the soybean (e.g., an extract of the soybean such as a lipid reduced soybean powder or filtered soymilk) or may contain the entire soybean (e.g., a ground powder of the soybean). The soybean extract may be in the form of a fluid (e.g., soymilk) or a solid (e.g., a soybean powder or soymilk powder).

The soybean extract may be soybean powder. Soybean powder may be made by grinding dry soybeans. The soybean powder may be lyophilized. Soymilk and soymilk powder are also useful soybean extracts. Soymilk is a combination of solids derived from soybeans and water, the mixture of which has some or all of the insoluble constituents filtered off. Soymilk powder is evaporated soymilk, which in one embodiment, is in a lyophilized or spray-dried form. Procedures for manufacturing soymilk include, but are not limited to, the following three procedures. First, soymilk may be made by placing soybeans into water to allow them to absorb the water. The swelled beans are then ground and additional water is then added. The mixture may then be filtered to remove any insoluble residue. Second, soymilk may also be prepared from soybean powder. Soybean powder is thoroughly mixed with water (e.g., for at least one hour), which may then be followed by a filtration process to remove insoluble residues. Third, soymilk can also be reconstituted from soymilk powder by adding water. The soymilk may comprise from about 1% to about 50%, by weight (e.g., from about 5% to about 20%, by weight) of solids from the soybean.

The known active ingredients of soybeans include, but not limiting to, isoflavones, phytoestrogens, genistein, daidzein, glycitein, saponins, and phytosterols. The soybean extracts useful in this invention may be produced from all soybean species, regardless of their geographic origin, sun exposure, harvest time and the like. However, specific strains, geographic origins or growth conditions might be preferred. For example, but not limiting to, soybean strains particularly rich in its Soybean Trypsin Inhibitor (STI) content or in isoflavone content, or growth conditions that result in STI or isoflavone enrichment in the bean, might be preferred.

In one embodiment, the soybean extract is a non-denatured soybean extract. "Denaturation" is defined in the Bantam Medical Dictionary (1990 edition) as "the change in the physical and the physiological properties of a protein, that are brought about by heat, X-rays or chemicals. These changes include loss of activity (in the case of enzymes) and loss (or alteration) of antigenicity (in the case of antigens)". What is meant by "non-denatured plant extract" is a product extracted or derived from a plant in which the processing for the derivation of such plant extract (e.g., the temperature, extraction media) did not eliminate its protease inhibitory activity. One such protease is trypsin. In one embodiment, the non-denatured state of the soybean extract of this invention is measured by the presence of an intact soybean trypsin inhibitor (STI) protein, or by its trypsin inhibitory activity.

It should be noted that the soybean extracts useful in the compositions of this invention may have a distinctive odor. If necessary, the odor of the extracts may be reduced by using soybean products derived from specific strains of soybeans known to produce reduced-odor, including, but not limited to, lipoxygenase-2-deficient beans and those having modified sugar profile, and the like. A process to reduce oxygen levels in the formulation may also reduce the odor. Various masking agents or fragrances may also be used to mask the odor. One way to make soymilk is to soak the soybeans in deionized or purified water for several hours, and grind them after they were fully hydrated, with the addition of small quantities of water. The grinding process allows the soybean milk to be extracted. After collection, the soybean milk may be filtered to remove any residual parts of the bean husk.

The soymilk used in the formulations described below can be fresh soymilk as described above, or may be made from soybean powder and water. The soybean powder is milled from soybeans and may also be lyophilized, spray dried, or freeze-dried and the resulting soymilk may or may not be filtered. Such prepared soymilk may have from about 1 to about 90% by weight dry soybean powder. Another example is the use of soymilk powder, made from lyophilized, spray dried or freeze-dried soymilk, with the addition of water and finished with or without filtration or homogenization. Other methods of soybean extraction could also be used to create the active ingredients in the formulations described below. For example, the active ingredients could be extracted from ground soybeans using ethanol/water mixtures, followed by the removal of the ethanol from the extract, in such ways that the serine protease inhibitory activity of the soybean will be retained, and preferably that the protein STI will remain intact.

In one embodiment, the soybean extracts utilized in the present invention have a microbial content of less than about 1,000 cfu per gram (such as less than about 100 cfu per gram) of the soybean extract.

The soybean extract may be exposed to gamma irradiation. The soybean extract may be exposed to from about 2 to about 30 kGy of gamma irradiation, such as from about 5 and about 10 kGy of gamma irradiation. Such treatment reduces the microbial content of the soybean extract, while maintaining its biological activity (e.g., serine protease inhibitory activity). The treatment of soybean extracts with gamma irradiation maintains the cosmetic elegance of the composition, such as maintained natural colors and does not induce significant malodors.

Other anti-microbial processes that also maintain the protease inhibitory activity of the soybean extract that can be practiced alone or in combination with gamma irradiation, include, but are not limited to, exposure to x-rays, high energy electron or proton beams, ultraviolet radiation, hydrostatic pressure, and addition of chemical agents possessing antimicrobial activity, and combinations thereof.

Other Materials

Various other materials may also be present in the compositions useful in the subject invention. These include humectants, proteins and polypeptides, preservatives and an alkaline agent. Examples of such agents are disclosed in the ICI Handbook, pp. 1650-1667. The compositions of the present invention may also contain chelating agents (e.g., EDTA) and preservatives (e.g., parabens). Examples of suitable preservatives and chelating agents are listed in pp. 1626 and 1654-55 of the ICI Handbook. In addition, the compositions useful herein can contain conventional cosmetic adjuvants, such as colorants such as dyes and pigments, opacifiers (e.g., titanium dioxide), and fragrances.

Mineral Water

The compositions of the present invention may be prepared using a mineral water, for example mineral water that has been naturally mineralized such as Evian® Mineral Water (Evian, France). In one embodiment, the mineral water has a mineralization of at least about 200 mg/L (e.g., from about 300 mg/L to about 1000 mg/L). In one embodiment, the mineral water contains at least about 10 mg/L of calcium and/or at least about 5 mg/L of magnesium.

Use

The composition according to the invention can be used to treat a variety of skin conditions, including but not, limited to acne. In one embodiment, the composition is used to treat other sebum disorders such as hyperlipidemia, hyperandrogenia, seborrhea, seborrheic dermatitis, seborrhea capitis, eczematoid seborrhea, seborrhea faciei, seborrhea oleosa, seborrhea sicca, seborrhea squamosa neonatorum, sebacious hyperplasia, Rosacea, follicular rash, demodex folliculorum, oily skin, Keratinous cyst, Pseudofolliculitis barbae and hypertrichosis.

The compositions of the present invention can also be used to reduce the appearance of pores and oil on the skin (e.g., the face, scalp, or hair).

The composition of the present invention can also be used to reduce acne lesions, comedones, or pimples, reduce the appearance of acne lesions, comedones, or pimples, reduces the appearance of acne breakouts and blemishes, prevent, control or regulate the appearance of acne breakouts and blemishes, and reduce breakouts and blemishes.

The composition of the present invention can also be used to promote the reduction in the appearance of oil on the skin, such as reducing the appearance of sebum, preventing, controlling or regulating the production of sebum, reducing sebum, reducing the appearance of oily/shiny skin, reducing the appearance of greasy skin, and reducing shine on the skin, hair, or scalp.

The composition and formulations containing such compositions of the present invention may be prepared using methodology that is well known by an artisan of ordinary skill.

EXAMPLE 1

In Vitro Sebocyte Lipogenesis Assay

Samples of facial skin obtained from subjects undergoing facelift surgeries were used. Upon arrival, the top 0.4 mm skin section, obtained by a dermatome was removed and the second 0.4 mm dermal section (previously shown to be rich in sebaceous glands) was used to isolate sebaceous cells. The tissue was digested with Dispase in Dulbecco's Modified Eagle Medium (DMEM) containing penicillin and streptomycin and 10% calf serum for 20 min at 37° C., and then with 0.3% trypsin/0.1% ethylenediaminetetraacetic acid (EDTA) in phosphate buffered saline (PBS) for 10 min at 37° C. Single cell suspensions were obtained by scraping the tissue vigorously with a scalpel blade. The released cells were seeded on a feeder layer of mitomycin C inactivated 3T3 fibroblasts and cultured in growth medium for 3 days at 37° C. The growth medium contained DMEM and F12 media (3:1), L-glutamine, sodium pyruvate, penicillin, streptomycin, 8% fetal bovine serum, 2% heat-inactivated human serum, epidermal growth factor, insulin, hydrocortisone, and either with or without cholera toxin (ChT). The cultures treated with ChT were shifted to a low-serum medium for 3 days and followed by a serum-free medium for another 7 days for the induction of lipid formation and storage, while the cultures without ChT treatment were maintained in growth medium (non-induced condition) for 10 days. The low-serum medium consisted of DMEM and F12 media (3:1) supplemented with L-glutamine, sodium pyruvate, penicillin, streptomycin, 2% heat-inactivated bovine serum and 2% heat-inactivated human serum, 1× insulin-transferrin-selenium, 1× trace elements. The serum-free medium contained DMEM and F12 media (3:1) supplemented with L-glutamine, sodium pyruvate, penicillin, streptomycin, 1× insulin-transferrin-selenium, 1× trace elements, 3,3',5-triiodo-L-thyronine sodium. For neutral lipid analysis by Nile Red staining, cells were grown in 96-well plates and for lipid analysis by thin layer chromatography, cells were grown in 6-well plates and harvested at the end of the culturing by scraping.

Testing Stimulators or Inhibitors of Sebocyte Differentiation and Lipid Production Hormones, mixture of hormones i.e. bovine pituitary extract or compounds to be tested were added to the culture at the beginning of serum free media addition. Two criteria were used to evaluate the effect of these materials on sebaceous cultures: 1) visual observations and 2) evaluation of sebaceous lipid accumulation and synthesis. The evaluation of lipid accumulation completed using the Nile red method. This method relies on visualization of neutral lipids by Nile red and quantitation by reading of fluorescence at 535 nm excitation, 580 nm emission using a plate reader. The lipid synthesis was evaluated by radioactive labeling using 14C acetate and quantified by Bio Rad Phosphoimager (Molecular Imager, FX) using 4.1 Software.

Morphological evaluation of lipid accumulation was easily recognized since the cells enlarged displayed lipid granules that in bright field light microscopy appeared as yellowish circles in the cells. Quantitation of accumulation/inhibition of neutral lipids in sebocytes was accomplished by Nile red binding assay. Briefly, following exposure of sebocytes to test compounds, the cells were allowed to interact with 1 μM Nile red in Hanks buffered saline solution containing DMSO and Pluronic F127. After 4 hours of incubation, washing and incubation overnight, the fluorescence was read at 535 nm excitation and 580 nm emission using a fluorescence plate reader and compared to an induction agent (i.e. cholera toxin). To determine whether the compounds had an inhibitory effect on cell growth, cell counts were performed.

Following the procedure described above, compounds of the present invention were tested for visual and Nile red evaluation of lipid accumulation, the results of which are depicted in Table 1.

TABLE 1

| Structure | % Reduction in Lipid Synthesis in Sebocytes [3 uM] | Structure | % Reduction in Lipid Synthesis in Sebocytes [3 uM] |
|---|---|---|---|
| 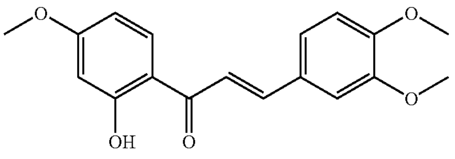 | 12.4 | 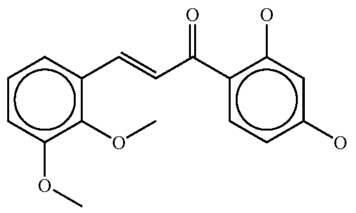 | Not Active |
| 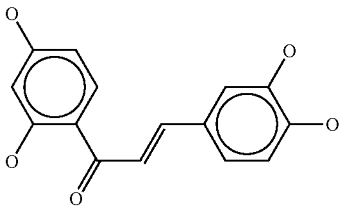 | 12.8 | 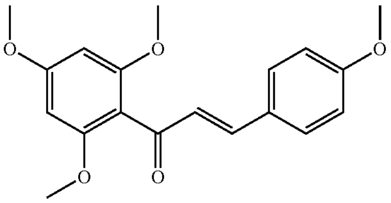 | Not Active |
| 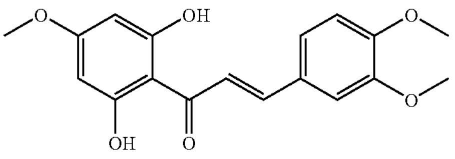 | 20.5 | 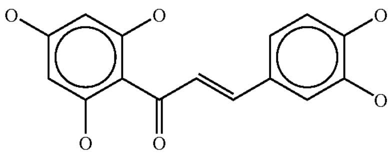 | Not Active |

TABLE 1-continued
| Structure | % Reduction in Lipid Synthesis in Sebocytes [3 uM] | Structure | % Reduction in Lipid Synthesis in Sebocytes [3 uM] |
|---|---|---|---|
| 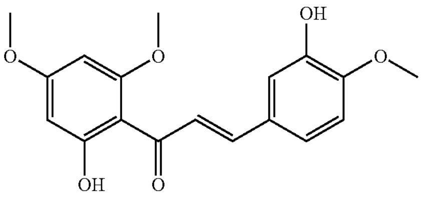 | 25.6 | 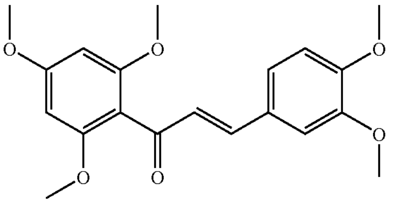 | Not Active |
| 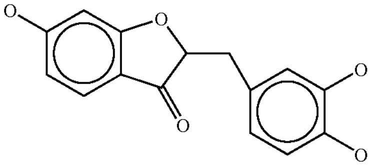 | 26.9 | 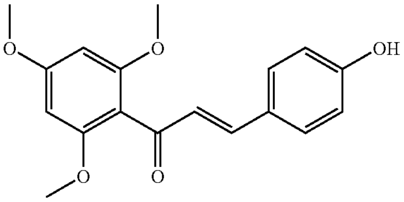 | Not Active |
| 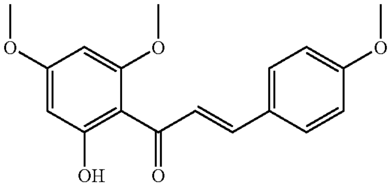 | 28.4 | 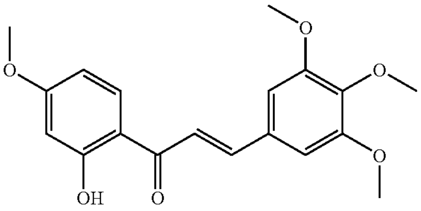 | Not Active |
| 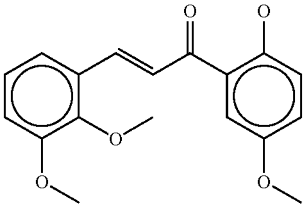 | 28.7 | 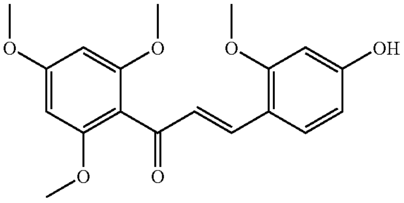 | Not Active |
| 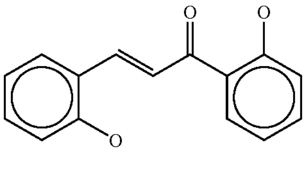 | 47.3 | 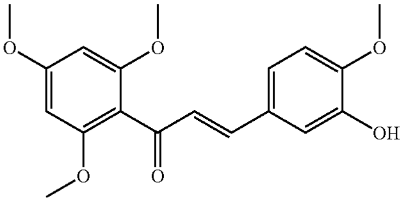 | Not Active |
| 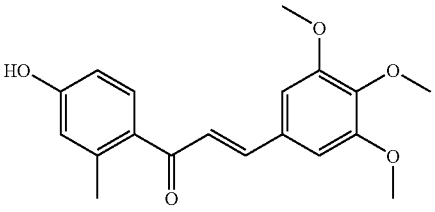 | Not Active | 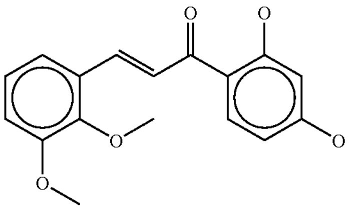 | Not Active |

TABLE 1-continued
| Structure | % Reduction in Lipid Synthesis in Sebocytes [3 uM] | Structure | % Reduction in Lipid Synthesis in Sebocytes [3 uM] |
|---|---|---|---|
| 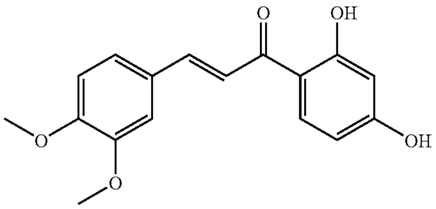 | Not Active | 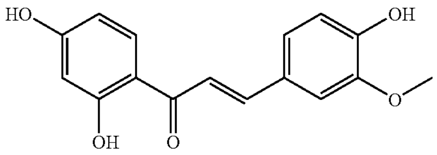 | Not Active |
| 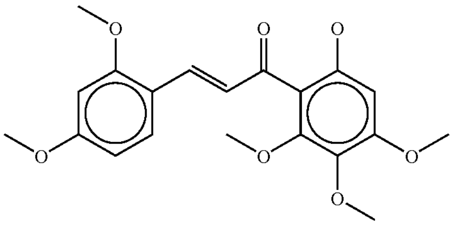 | Not Active | 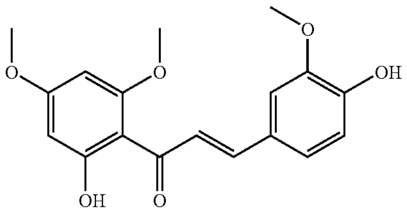 | Not Active |
| 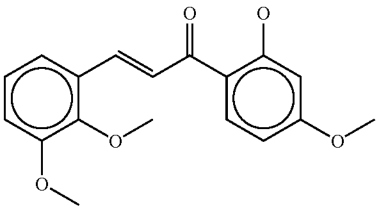 | Not Active | 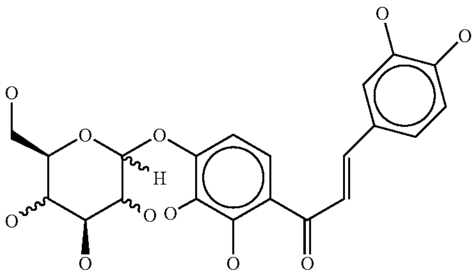 | Not Active |
| 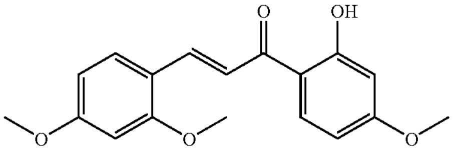 | Not Active | 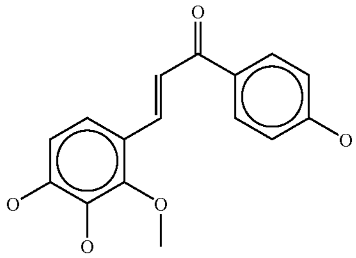 | Not Active |
| 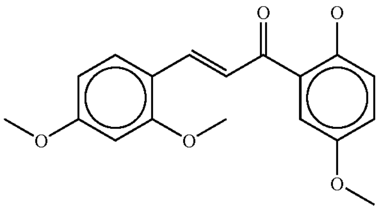 | Not Active | 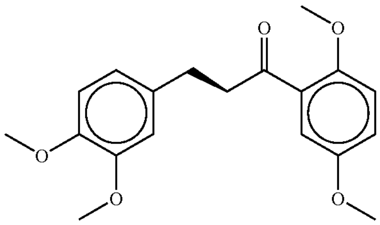 | Not Active |
| 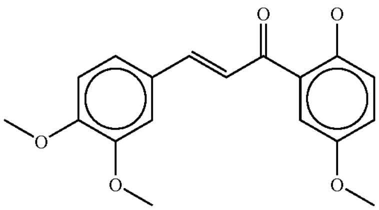 | Not Active | 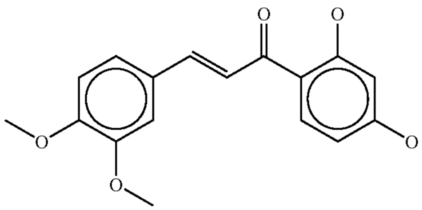 | Not Active |

In the same assay, synergism between the chalcones of the present invention and Green Tea extract was also found (See Table 2).

TABLE 2

| Green Tea Extract Concentration | 2,2'-dihydroxy-chalcone Concentration | % Cholera Toxin Reduction |
|---|---|---|
| 0.0 μg/mL | 3.0 μM | 50.8 |
| 0.0 μg/mL | 1.0 μM | 38.2 |
| 0.0 μg/mL | 0.3 μM | 14.3 |
| 1.25 μg/mL | 0 μM | 13.3 |
| 2.5 μg/mL | 0 μM | 24.2 |
| 1.25 μg/mL | 3.0 μM | 71.1 |
| 2.5 μg/mL | 3.0 μM | 84.1 |
| 1.25 μg/mL | 1.0 μM | 63.3 |
| 2.5 μg/mL | 1.0 μM | 77.1 |
| 1.25 μg/mL | 0.3 μM | 46.5 |
| 2.5 μg/mL | 0.3 μM | 65.9 |

What is claimed is:

1. A method of treating acne or reducing the appearance of oil or pores on the skin, said method comprising administering to skin in need of such treatment a composition comprising a chalcone, wherein said chalcone is 2'-hydroxy-2,3,5'-trimethoxychalcone, an enantiomer thereof, or a diastereoisomer thereof, or a cosmetically acceptable salt thereof.

2. A method of claim 1, wherein said method comprises treating acne.

3. A method of claim 1, wherein said composition further comprises salicylic acid or benzoyl peroxide.

4. A method of claim 1 wherein said composition further comprises a catechin.

5. A method of claim 4 wherein said wherein said catechin is selected from the group consisting of catechin, catechin gallate, epicatechin, gallocatechin, gallocatechin gallate, epigallocatechin, epicatechin gallate, and epigallocatechin gallate.

6. A method of claim 5, wherein said composition further comprises salicylic acid or benzoyl peroxide.

7. A method of claim 4, wherein said composition further comprises salicylic acid or benzoyl peroxide.

* * * * *